United States Patent [19]
MacFarland et al.

[11] 4,358,949
[45] Nov. 16, 1982

[54] ARGON PURITY TESTER

[75] Inventors: James M. MacFarland, Frederica; Bernard W. Kappe, Wyoming, both of Del.

[73] Assignee: The United States of America as represented by the Secretary of the Air Force, Washington, D.C.

[21] Appl. No.: 206,412

[22] Filed: Nov. 13, 1980

[51] Int. Cl.³ ............................................. G01N 27/16
[52] U.S. Cl. ...................................... 73/23; 73/27 R; 340/632
[58] Field of Search ..................... 73/23, 25, 26, 27 R; 422/94, 86; 340/632

[56] References Cited
U.S. PATENT DOCUMENTS

| | | | |
|---|---|---|---|
| 1,889,890 | 12/1932 | Erickson | 422/94 |
| 1,995,870 | 3/1935 | Stone | 340/632 |
| 2,601,272 | 6/1952 | Frost, Jr. | 73/23 |
| 2,774,652 | 12/1956 | Vonnegut | 340/632 |
| 3,194,054 | 7/1965 | Deaton et al. | 73/25 |
| 3,662,588 | 5/1972 | Emerson et al. | 73/23 |
| 3,691,818 | 9/1972 | Emerson et al. | 73/23 |

OTHER PUBLICATIONS

*Gas Chromatography*, Edited by V. J. Coates et al., Chap. 15, pp. 131-134, 1958.
*Thermal Conductivity Detector Elements for Gas Analysis From GOW-MAC*, Bulletin SB-13, pp. 1-7, 1971.

*Primary Examiner*—Stephen A. Kreitman
*Attorney, Agent, or Firm*—Donald J. Singer; Jacob N. Erlich

[57] ABSTRACT

An inert gas purity tester having a housing made of transparent material and in which is located a thin wire tungsten filament. The filament is electrically connected to a variable electrical power source from, for example, an inert gas welding apparatus in order to provide a regulated flow of current to pass through the filament. The power source is then regulated until the filament glows white. The housing also has formed therein an inlet and outlet for allowing the flow of inert gas to pass therethrough. During the passage of gas through the housing, a trace of smoke detected at the white glowing filament indicates the presence of an impurity of oxygen within the inert gas such as argon. Viewing is continued until no more smoke is detected and it is therefore established that the impurity is no longer present in the gas. Thereafter, inert gas welding can be successfully undertaken.

9 Claims, 1 Drawing Figure

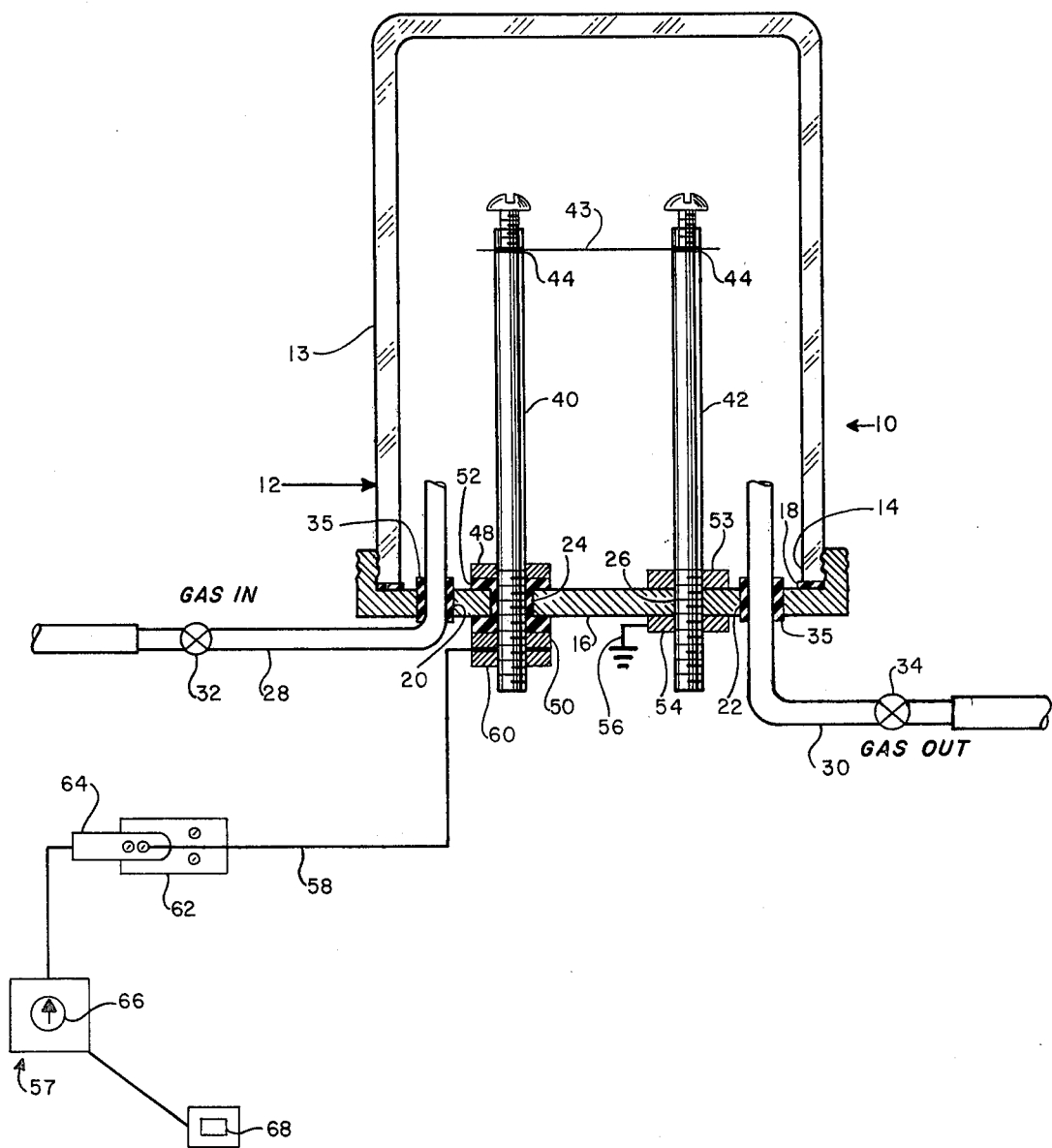

ARGON PURITY TESTER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to gas purity testers or analyzers and, more particularly, to an argon purity tester which can be utilized in conjunction with an inert gas welding chamber.

As the need increases for lighter and/or stronger materials in areas such as aerospace construction, the joining together of these light weight materials, such as aluminum or titanium, has led to the increased use of inert gas welding. Unfortunately in the welding of titanium, for example, impurities found in the welding environment of argon can cause considerable damage to the weld formed in the material. An example of such an impurity is oxygen, the pressure of which in the argon can create cracks in the area of the weld.

During the welding procedure, testing of the welding environment is extremely difficult. In most instances it becomes necessary to completely shut down the operation of the welding chamber during the testing of the argon or other inert gas used in the welding operation. In other instances, to measure the purity of such inert gas welding systems, highly complex machinery must be utilized in order to detect impurities within the gas.

There arises a great need in inert gas welding field for a purity tester which is not only operable in combination with the welding system but which can also be used directly with the argon or inert gas cylinders and which is accurate, economical and high reliable during operation.

SUMMARY OF THE INVENTION

The instant invention overcomes the problems encountered in the past by providing an inert gas tester, and, more particularly, an argon purity tester which is highly reliable in operation, easily maintained and yet capable of detecting impurities in the range of one part oxygen to one billion parts argon.

The argon purity tester of this invention is made up of a housing in the form of a transparent cylindrically-shaped member, made preferably of glass, and open at one end thereof. Completing the housing is a base plate which is secured to and encloses the open end of the transparent member.

Formed within the base plate are four openings. Two of the openings permit the passage therethrough of an inlet and outlet line while the other two openings have located therein a pair of conductive rods. The conductive rods, preferably made of brass, are situated within the transparent member. One of the brass rods is insulated from the surrounding base plate and connected to any suitable power source which, in this instance, may take the form of the power source of the welding apparatus utilized within an inert gas welding system. The other brass rod is also secured to the base plate can be grounded either by independent means or by having the base plate secured directly to a grounded portion of an inert gas welding chamber.

Situated and operably connected between the two brass rods is a thin wire filament, preferably made of tungsten, approximately 0.040 inches thick. The tungsten filament is held in position by being inserted into a pair of adjacent slots located within each of the brass rods. A pair of securing elements in the form of set screws securely fasten the thin filament in position within each brass rod.

Although this invention is capable of utilization with a number of inert gases, the following operation will be explained with respect to argon, the gas with which the purity tester of this invention finds its main utility. During the argon purity testing operation an argon cylinder or a line from an inert gas welding system is connected to the gas inlet line of the purity tester of this invention. Once in position, the flow of argon is adjusted so as to flow through the transparent member of the housing at approximately 40 cubic feet per hour. This flow ordinarily takes place for about 90 to 120 seconds before actual testing commences.

By the application of the proper amount of current to the tungsten filament, the tungsten filament is made to glow white. If the tungsten filament glows red or orange, insufficient power has been applied to test for impurities within the argon. Too much power will produce a brilliant white to a dazzling white and melt the tungsten filament. When the tungsten filament is in fact at the desired white glow, if there is any impurity, in the form of oxygen, within the argon, a small amount of smoke is produced by the tungsten filament. Testing is continued until the tungsten filament glows white and no more smoke is visible. At this time the absolute purity of the argon is established. Inert gas welding within the inert gas welding system or inert gas welding from the argon cylinder can now take place.

It is therefore an object of this invention to provide a tester which is capable of determining impurities such as oxygen within an inert gas such as argon.

It is another object of this invention to provide an argon purity tester which utilizes in the construction thereof durable and replaceable elements.

It is still a further object of this invention to provide an argon purity tester which includes therein the utilization of a transparent, easily cleaned member for observation of a signal indicating impurities within the inert gas being tested.

It is still another object of this invention to provide an argon purity tester which does not require the utilization of its own power source but can rely upon on external power source such as the power source of an inert gas welding system.

It is still another object of this invention to provide an argon purity tester which can be easily utilized in conjunction with an inert gas welding chamber.

It is still a further object of this invention to provide an argon purity tester which is economical to produce and which utilizes conventional components which are readily adaptable to mass producing manufacturing techniques.

For a better understanding of the present invention, together with other and further objects thereof, reference is made to the following description taken in conjunction with the accompanying drawing and its scope will be pointed out in the appended claims.

BRIEF DESCRIPTION OF THE DRAWING

The only FIGURE of the drawing is a side elevational view of the argon purity tester of this invention shown partly in cross-section.

DESCRIPTION OF THE PREFERRED EMBODIMENT

Reference is now made to the only FIGURE of the drawing which clearly illustrates the argon purity tester 10 of this invention. Since the primary function of tester 10 of the present invention is for detecting impurities such as oxygen within argon, the tester 10 will be referred to as an argon purity tester. However, it should be realized that the purity of other inert gases can be established within the scope of this invention.

Tester 10 is formed of a housing 12 made up of a transparent member 13 open at one end 14 thereof and enclosed by a base plate 16. Transparent member 13 may be of any suitable configuration such as being cylindrically-shaped. The transparent material may be made of any suitable transparent material such as glass or plastic. Base plate 16 may be made of any suitable material such as steel and can be secured to cylindrically-shaped member 13 in any conventional manner such as by being screwed thereon. Any suitable gasket 18 or sealing member can be interposed between cylindrical member 13 and base plate 16.

More specifically, base plate 16 has formed therein four apertures 20, 22, 24 and 26. Apertures 20 and 22 allow the introduction therethrough of an inlet line 28 and an outlet line 30, respectively. These lines may be made of any suitable metal or plastic tubing and may include, if desired, any conventional valves 32 and 34, respectively, therein. A sealing member in the form of gasket 35 made of, for example, silicone is interposed between inlet and outlet lines 28 and 30 and base plate 16.

Situated within openings 24 and 26, respectively, are a pair of conductive rods 40 and 42, made preferably of brass. Each of the rods 40 and 42 have formed adjacent one end thereof a slot 44. Associated with each slot 44 is a mounting or holding element in the form of set screw 46 which is utilized to fixedly position between rods 40 and 42 a thin wire filament 43 made preferably of tungsten and having a thickness or diameter of, for example, 0.040 inches. The other ends of rods 40 and 42 protrude through base plate 16. Rods 40 and 42 are secured to base plate 16 in a manner to be described in detail hereinbelow.

For example, one of the brass rods 40 is secured to base plate 16 by a pair of conventional securing means in the form of nuts 48 and 50 and an insulating bushing 52 formed therebetween. Bushing 52 acts as an insulation between brass rod 40 and base plate 16. Brass rod 42 is secured directly to base plate 16 by means of any suitable securing means such as nuts 53 and 54. Base plate 16 may be secured in any conventional manner to a grounded surface on, for example, an inert gas welding chamber or, if used independently of the welding chamber, nut 54 can have secured thereto any suitable grounding wire 56.

Referring once again to conductive rod 40. Rod 40 is operably connected to a suitable power source 57 which may, in this instance, take the form of the power source 57 from the welding apparatus of any conventional inert gas welding system (not shown). Interconnecting power source 57 to brass rod 40 is a conductive element in the form of a wire 58 which is connected at one end thereof to rod 40 by being secured between nut 50 and another nut 60 which is also attached to brass rod 40. At the other end of wire 58 is an insulator element 62 which mounts thereon a copper strip 64 thereby allowing for the interconnection of power source 57 to wire 58.

MODE OF OPERATION

Operation of the argon purity tester 10 of this invention commences when the line of an inert gas welding system or an inert gas cylinder, which, for example, contains argon is connected to the inert line 28 of the purity tester 10 of this invention. Once connected thereto argon (or any other suitable inert gas) can flow at an adjusted rate of, for example, 40 cubic feet per hour through the argon purity tester 10 of this invention. During a waiting period of approximately 90 to 120 seconds, the power source 57 may be connected to the copper strip 64 of insulator element 61 and adjustment of the argon purity tester 10 of this invention can take place.

Adjustment or purity tester 10 takes place in the following manner. Initially, a suitable power source 57 of a welding machine (not shown) is set up to power purity tester 10. During this initial phase of operation it necessary to adjust the power output of the power source 57 by moving the dial or control 66 therein to its lowest position and to press the remote control foot pedal or switch 68 to its fullest on position. During this procedure, the power is gradually increased by appropriate adjustment of dial or control 66. This procedure is undertaken with foot pedal or switch 68 in its fully on position. Increasing the power increases the current flowing through filament 43 until the tungsten filament 43 glows white. If the tungsten filament 43 glows red or orange insufficient power has been provided to tester 10 and the filament is insufficiently hot for testing. If too much power is given to tester 10 of this invention, filament 43 will glow a brilliant white to a dazzling white and melt. Desirable power is such that when filament 43 is glowing white and a trace of red has just disappeared. It is at this setting at which the argon purity tester 10 of this invention is fully operable.

Thereafter, during the flow of an inert gas such as argon through tester 10, if a trace of smoke is detected from the glowing white tungsten filament 43, it is evident that an impurity such as oxygen exists within the argon or other inert gas passing through housing 12 or purity tester 10 of this invention. In fact, the purity tester 10 of this invention provides a smoke signal when even a minute quantity of oxygen is present, that is, in the range of one part oxygen to one billion parts argon. When no more smoke emanates from tungsten filament 43 and it is merely glowing white the argon passing through tester 10 is pure and void of impurities such as oxygen which would damage the welding of, for example, titanium.

The argon purity tester 10 of this invention can be used directly within an inert gas welding system or with the argon cylinders for use in an inert gas welding system. Since the elements making up this invention are easily obtainable and since the tester 10 itself can be disassembled quite easily, it can be operated in a reliable and efficient manner at the site of the welding operation. Furthermore, the accuracy obtainable in determining an impurity such as oxygen within an inert gas such as argon is well within required specifications for the inert gas welding of titanium. Additionally, the tester 10 of this invention can be run simultaneousy with the welding operation by the operator of the welding equipment and does not, therefore, require additional operators for its use.

Although this invention has been described with reference to a particular embodiment, it will be understood to those skilled in the art that this invention is also capable of further and other embodiments within the spirit and scope of the appended claims.

We claim:

1. An inert gas purity tester comprising a housing, said housing including a transparent member open at one end thereof and a base plate removably sealing said open end of said transparent member; means located within said housing for passing a current therethrough, said current passing means including a pair of conductive elements and a thin wire filament electrically connected therebetween and wherein one of said conductive elements is grounded; means operably connected to said housing for passing said inert gas through said housing at a preselected flow rate; and means operably connected to the other of said conductive elements for providing sufficient current to pass through said thin wire element in order to cause said thin wire filament to glow white, said current providing means including an electrical power source having means for controlling the power output therefrom, means for removably connecting said power source to said other conductive element, and means connected to said power source for turning said power source to its fully on position whereby the presence of an impurity within said inert gas passing through said housing causes smoke to appear adjacent said thin wire filament thereby indicating the existance of said impurity within said inert gas.

2. An inert gas purity tester as defined in claim 1 wherein said inert gas passing means comprises a first and a second opening in said base plate, a gas inlet line operably connected to said first opening and a gas outlet line operably connected to said second opening.

3. An inert gas purity tester as defined in claim 2 wherein each of said conductive elements has a slot formed therein, said thin wire filament being situated within said slot in each of said conductive elements and means operably connected to each of said conductive elements for securing said thin wire filament thereto.

4. An inert gas purity tester as defined in claim 3 wherein said thin wire filament is made of tungsten and is approximately 0.040 inches thick.

5. An inert gas purity tester as defined in claim 4 wherein said base plate is made of a conductive material and has a third and fourth opening therein, said one conductive element passing through said third opening and means connected to said one conductive element for securing said one conductive element to said base plate, said other conductive element passing through said fourth opening, means interposed betwen said other conductive element and said base plate for insulating said other conductive element from said base plate and means connected to said other conductive element for securing said other conductive element to said base plate.

6. An inert gas purity tester as defined in claim 5 wherein said inert gas purity tester is used in combination with an inert gas welding system and said power source forms part of said welding system.

7. A method of testing an inert gas for an impurity within said gas prior to commencing with a welding procedure within said inert gas comprising the following steps:

(a) connecting an inert gas source to a transparent housing of a purity tester containing a thin wire filament capable of having current pass therethrough;

(b) connecting a power source used for said welding procedure to said thin wire filament;

(c) adjusting said purity tester prior to passing said inert gas therethrough by turning said power source to its fully on position while simultaneously increasing the power output therefrom in order to adjust the amount of current passing through said thin wire filament until said thin wire filament glows white when said power is in its fully on position; and (d) passing said inert gas through said housing of said purity tester in order to detect a trace of smoke adjaent said filament thereby establishing the presence of said impurity within said inert gas.

8. A method of testing an inert gas for an impurity within said gas as defined in claim 7 further comprising the step of regulating the passing of said inert gas through said housing to the rate of approximately 40 cubic feet per hour.

9. A method of testing an inert gas for an impurity within said gas as defined in claim 8 further comprising the step of continually viewing said filament until said trace of smoke no longer appears adjacent said filament.

* * * * *